United States Patent [19]

Greenwald

[11] 4,128,425
[45] Dec. 5, 1978

[54] PHOTOGRAPHIC DEVELOPERS

[75] Inventor: Richard B. Greenwald, Cambridge, Mass.

[73] Assignee: Polaroid Corporation, Cambridge, Mass.

[21] Appl. No.: 794,480

[22] Filed: May 6, 1977

[51] Int. Cl.² .......................... G03C 5/30; G03C 1/06; G03C 5/54
[52] U.S. Cl. .................................... 96/66 HD; 96/3; 96/29 R; 96/66 R; 96/95
[58] Field of Search ................ 96/66 R, 66 HD, 29 R, 96/3, 95, 56.5

[56] References Cited

U.S. PATENT DOCUMENTS

| 930,091 | 8/1909 | Scheitlin | 96/66 HD |
| 2,163,781 | 6/1939 | Eggert | 96/66 HD |
| 3,012,884 | 12/1961 | deRamaix | 96/9 |
| 3,767,400 | 10/1973 | Hayakawa et al. | 96/35.1 |
| 4,061,498 | 12/1977 | Monbaliu | 96/56.5 |

OTHER PUBLICATIONS

Wiley & Wiley, Pyrazolones, Pyrazolidones & Derivatives, 1964, pp. 46-64, 76-81, 115-122, 123-138.

Primary Examiner—Mary F. Kelley
Attorney, Agent, or Firm—Gaetano D. Maccarone; Doris M. Bennett

[57] ABSTRACT

In one embodiment, the present invention relates to pyrazolidine derivatives, some of which are novel compounds, all of which are represented by the formula:

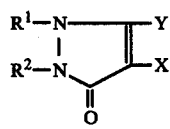

wherein $R^1$ and $R^2$ taken individually, the same or different, are each hydrocarbon moieties containing up to about 20 carbon atoms selected from alkyl, aryl, aralkyl and alkaryl, which moieties may be unsubstituted or substituted with a substituent selected from carboalkoxyalkyl, aryl, alkyl, alkoxy, hydroalkyl, aminoalkyl, ketalalkyl and acetalalkyl, and $R^1$ and $R^2$ taken together represent the carbon atoms necessary to complete a cyclic moiety selected from:

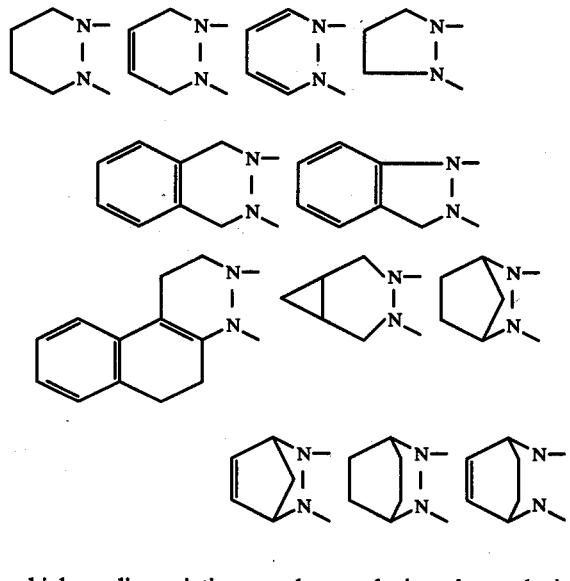

which cyclic moieties may be unsubstituted or substituted with the above-identified substituents; Y is —OH or —NH₂; and X is —OH, —NH₂, —NH₂.Z where Z is a salt, or —NHR where R is alkyl or aryl.

In another embodiment, the present invention is directed to the use of the above-denoted class of compounds as photographic silver halide developing agents and to photographic processes, products and compositions employing the same.

12 Claims, No Drawings

1

PHOTOGRAPHIC DEVELOPERS

BACKGROUND OF THE INVENTION

1. Field of the Invention

This invention relates to photography and to novel chemical compounds useful therein. More particularly, it relates to novel chemical compounds useful in the development of photosensitive silver halide materials and to photographic products, processes and compositions employing the same.

2. Description of the Prior Art

In the photographic art, developing agents are employed to convert the exposed silver halide to metallic silver. The most common of these developers has been, until recent years, hydroquinone and hydroquinone derivatives, para-aminophenol and para-phenylenediamine. However, there has been an increasing interest in recent years in heterocyclic developing agents, i.e., developing agents containing a heterocyclic ring as part of their structure. Some of these developing agents have the conventional hydroxyl or amino developing groups substituted on adjacent carbon atoms of a heterocyclic ring to provide structures similar to those of the developing agents in the aliphatic and aromatic series. Still other heterocyclic developing agents as exemplified by 1-phenyl-3-pyrazolidinimine and 1-phenyl-3-pyrazolidone (commercially available under the trademark "Phenidone") have one of the functional developing groups included as part of the heterocyclic ring. 1-Phenyl-3-pyrazolidinimine forms the subject matter of British Pat. No. 757,840 and 1-phenyl-3-pyrazolidone and its 4,4-dialkyl derivatives form the subject matter of U.S. Pat. Nos. 2,289,367 and 2,772,282 respectively. The best known of these developing substances, viz 1-phenyl-3-pyrazolidone itself possesses only poor developing properties as far as its development in aqueous medium is concerned [J. D. Kendall, British Journal of Photography (1951) 539]. The commercial significance of the above-identified developing agents in general, therefore, rests primarily in their ability to form superadditive mixtures with other developing agents, for example, hydroquinones.

The present invention is concerned with novel silver halide developing agents some of which are in addition, novel heterocyclic compounds, and all of which are useful in conventional and in diffusion transfer photography, both black-and-white and color.

SUMMARY OF THE INVENTION

It is, therefore, one object of the present invention to provide photographic products, processes and compositions employing the subject compounds for development of photosensitive silver halide materials.

It is yet another object of the present invention to provide novel heterocyclic compounds useful for the the above-identified objective.

These and other objects of the present invention will be more readily apparent in consideration of the ensuing discussion.

The invention accordingly comprises the processes involving the several steps and the relation and order of one or more of such steps with respect to each of the others, and the products and compositions possessing the features, properties and the relation of elements which are exemplified in the following detailed disclosure, and the scope of the application of which will be indicated in the claims.

For a fuller understanding of the nature and objects of the invention, reference should be had to the following detailed description.

DETAILED DESCRIPTION OF THE INVENTION

According to the present invention, it has been found that the compounds as represented in Formula I below, some of which are new heterocyclic compounds per se, are useful as photographic silver halide developing agents and may be used alone or in combination with developing agents such as hydroquinone and substituted hydroquinones, phenols, 1,4-diaminobenzenes, ascorbic acid and its derivatives, hydroxylamines and the like.

The novel developing agents of the present invention are represented by the formula:

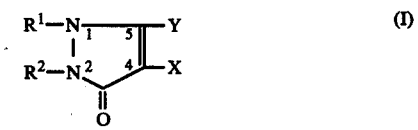

wherein $R^1$ and $R^2$ taken individually, the same or different, are each hydrocarbon moieties containing up to 20 carbon atoms selected from alkyl, preferably a lower alkyl containing 1 to 4 carbon atoms such as methyl, ethyl, propyl, isopropyl, butyl, etc.; aryl, preferably pyridyl, pyridyl-N-oxide or phenyl; aralkyl, preferably pyridylalkyl, pyridyl-N-oxide alkyl or phenylalkyl and particularly phenylalkyl wherein the alkyl portion contains 1 to 4 carbon atoms, alkaryl, preferably alkylpyridyl, alkylpyridyl-N-oxide or alkylphenyl wherein the alkyl portion contains 1 to 4 carbon atoms, which moieties may be unsubstituted or substituted with a substituent selected from carboalkoxyalkyl, aryl, alkyl, alkoxy, hydroxyalkyl, aminoalkyl, ketalalkyl and acetalalkyl, and $R^1$ and $R^2$ when taken together represent the carbon atoms necessary to complete a cyclic moiety, for example, a 5 to 7 carbon cycloalkyl, a bicycloalkyl or the like, which cyclic moiety is selected from:

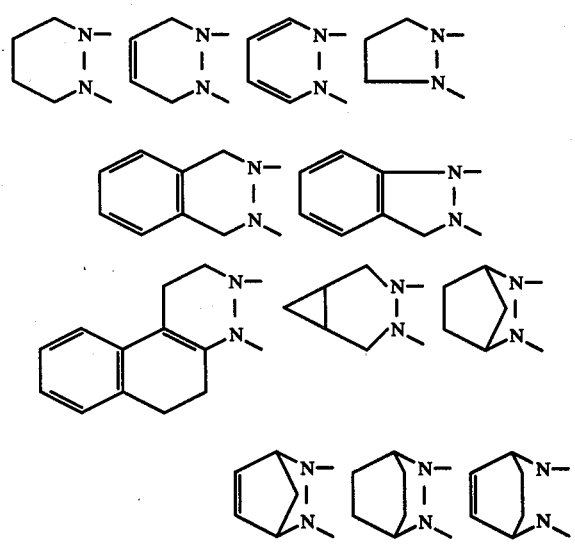

which cyclic moieties may be unsubstituted or substituted with a substituent selected from carboalkoxyalkyl, aryl, alkyl, alkoxy, hydroxyalkyl, aminoalkyl, ketalalkyl and acetalalkyl; Y is —OH or —NH$_2$; and X is —OH, —NH$_2$, —NH$_2$.Z where Z is a salt, or —NHR where R is alkyl, preferably a lower alkyl having 1 to 4 carbon atoms, substituted alkyl, or aryl. In a preferred embodiment of this invention, R$^1$ and R$^2$ form a compound where X and Y are dissimilar substituents, preferably X is NH$_2$ and Y is OH. In addition, it will be appreciated that when Y is hydroxy such compounds also may be written in the keto form as follows:

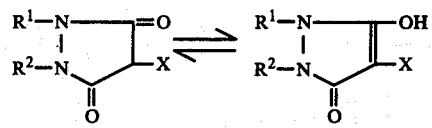

Specific examples of compounds useful in the present invention are as follows:

(1)
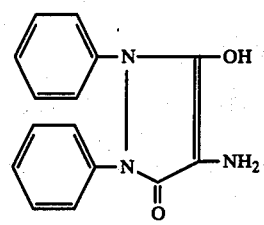

(2)
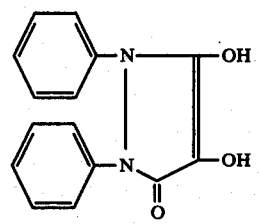

(3)
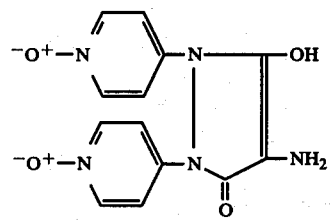

(4)
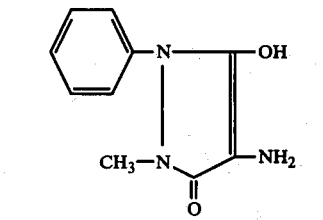

(5)
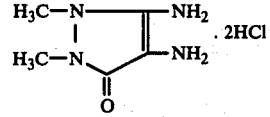

(6)
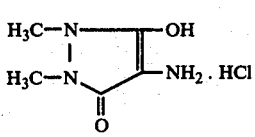

-continued

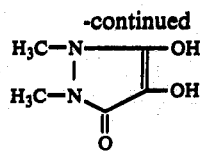

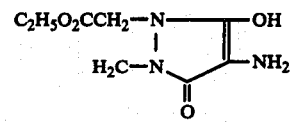

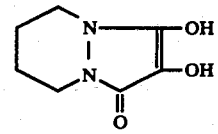

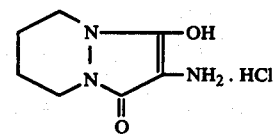

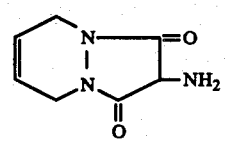

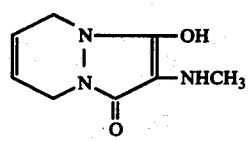

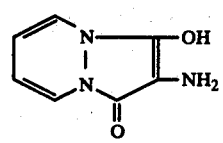

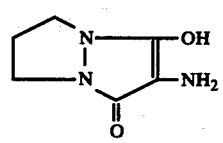

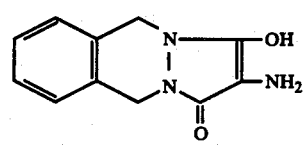

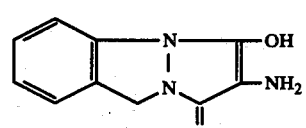

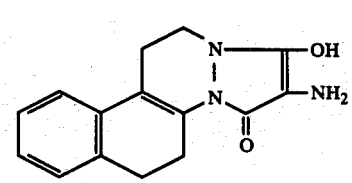

-continued

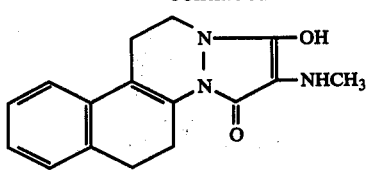 (18)

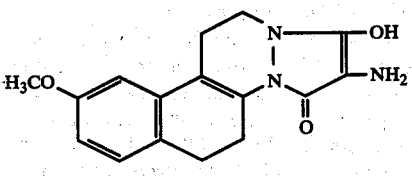 (19)

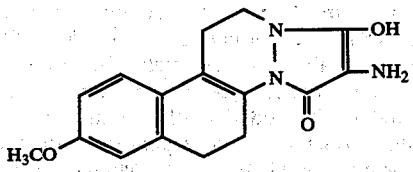 (20)

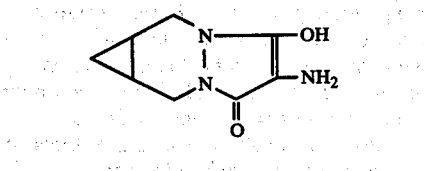 (21)

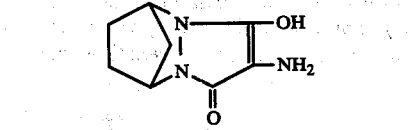 (22)

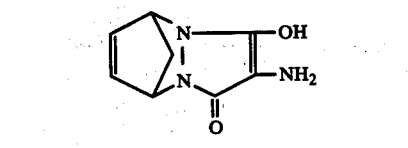 (23)

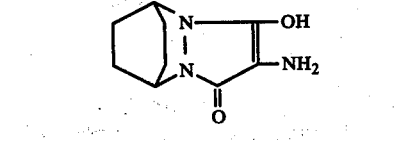 (24)

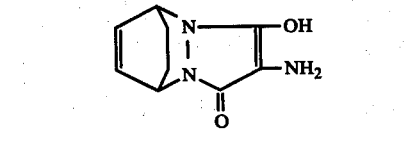 (25)

The novel compounds per se of the present invention, are encompassed by formula I and represented by the formula:

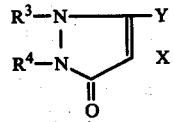

wherein X and Y are as defined above, $R^3$ and $R^4$ are the same as $R^1$ and $R^2$ provided that when Y is —OH and X is either —OH or —$NH_2$, $R^3$ and $R^4$ taken individually are each not phenyl.

The 3:5-dioxopyrazolidine developing agents of this invention may be synthesized according to several techniques, some of the intermediate steps in these syntheses having been reported in the literature as applied to different classes of compounds. These literature references are as follows:

(a) Helvetica Chimica Acta, 44, p. 236 par. 5b, (1961) which disclosed combining diphenyl hydrazine with a substituted malonic acid in the presence of N,N'-dicyclohexylcarbodiimide in dioxane.

(b) Monatshefte für Chemie, 99, p. 605, (1968) which discloses condensation of 1,2-dimethylhydrazine with dimethyl malonate;

(c) Ber. 73, 820 (1940) which discloses treatment of the sodium salt of diethyl malonate with a hydrazine.

A summary of the three principle methods of synthesizing the 4-amino compounds of this invention follows:

(I) The appropriate hydrazine (1) is first condensed with a dialkyl malonate such as dimethyl malonate at above ambient temperatures. The resultant diketo form of the 3,5-pyrazolidinedione (2) is then oximated for formation of the respective and more complex pyrazolidinetrione oxime hydrate (3). The latter reaction may be accomplished in either of the following ways:

(a) a nitrosating agent such as sodium nitrite in aqueous solution may be added to an acidic solution of (2) such as 90% acetic acid or;

(b) an aqueous acid such as dilute hydrochloric acid is combined with the specific pyrazolidinedione (2) and to it added the aqueous solution of nitrosating agent.

After either (a) or (b) is performed to yield the oxime (3) which is subsequently isolated, the oxime is thereafter reduced conventionally by the use of hydrogen, 10% palladium on carbon in a protic solvent, for example, an alcohol such as ethanol or methanol or the like. However, where the product is poorly soluble in aqueous systems a reducing agent such as sodium dithionite is preferably employed due to the improved yield of the final disubstituted 3:5-dioxopyrazolidine product (4).

The reaction may best be summarized by reference to the following reaction sequence:

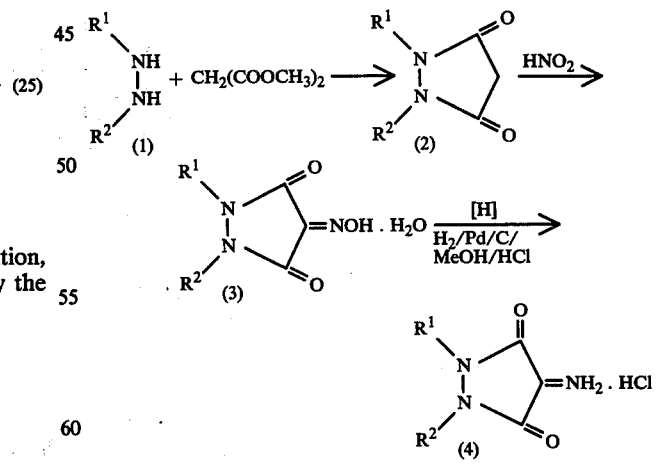

$R^1$ and $R^2$ are as defined above.

(II) The appropriate hydrazine (1) instead of being condensed with dimethyl malonate is combined with malonic acid in the presence of N,N'-dicyclohexylcarbodiimide (hereinafter referred to as "DCC") and/or 1-ethoxycarbonyl-2-ethoxy-1,2-dihydroquinoline (hereinafter referred to as EEDQ) as a condensing agent to yield the diketo form of the disubstituted 3,5-pyrazolidinedione (5).

Once the diketo compound (5) is obtained [which corresponds to (2) in reaction sequence (I)] the final 3:5-dioxopyrazolidine compound (7) is derived by the same technique (s) as followed in reaction sequence (I). Thus, the diketo compound (5) is converted to the oxime (6) [which corresponds to (3) in reaction sequence (I)] which oxime hydrate is thereafter hydrogenated to afford the novel developing agent (7), i.e., the diketo compound is oximated and reduced by catalytic hydrogenation or by the use of a reducing agent such as sodium dithionite. This reaction sequence may be summarized as follows:

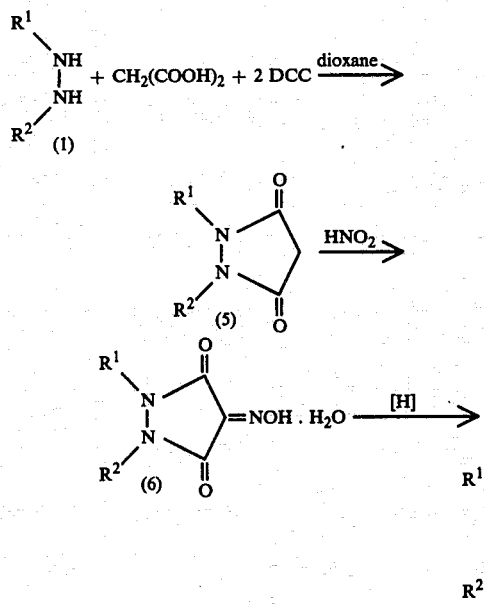

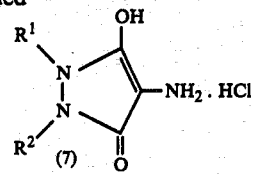

$R^1$ and $R^2$ are as defined previously.

(III) The final method of synthesizing the novel developers of this invention is to combine the appropriate hydrazine (1) with an enamine, for example, ethyl β-amino-βethoxyacrylate in the presence of a protic solvent such as ethanol. The resultant 1,2-disubstituted 3-amino-5-pyrazolone (8) is hydrolyzed in the presence of an acid to yield the 3,5-pyrazolidinedione compound (9) which is isolated corresponding to (2) and (5) in reaction sequence I and II, respectively. The solid (9) is combined with an aqueous acid, for example, 90% acetic acid and nitrite added to the mixture such as sodium nitrite to obtain the corresponding pyrazolidinetrione oxime compound (10) corresponding to (3) and (6) in reaction sequences I and II, respectively. The oxime (10) is reduced to yield the novel 3:5-dioxopyrazolidine developing agents (11) of this invention. Where it is desired to prepare a 3,4-diamino compound, an acetic acid solution of compound (8) is treated with sodium nitrite either as a solid in small quantities or in aqueous solution to give the oxime hydrate (12) which is catalytically reduced to yield the product (13). The following diagram summarizes this reaction sequence.

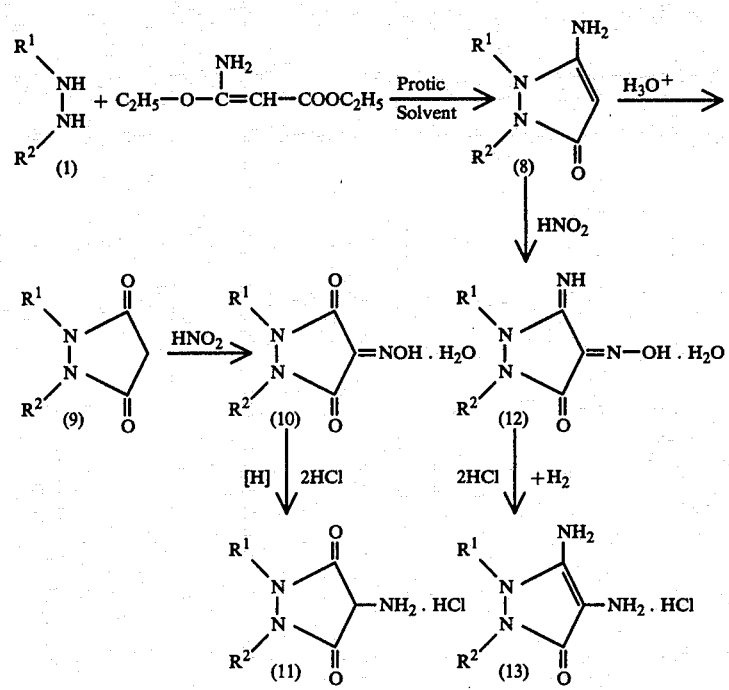

$R^1$ and $R^2$ are as defined previously.

There are three basic methods of synthesizing the 4-amino salt compounds of the present invention. They are as follows:

(I) The 3:5-dioxopyrazolidine compounds, e.g., the 1,2-dimethyl or the tetramethylene compounds may be combined with the appropriate reactant, viz. an acid such as hydrochloric acid, sulfuric acid or the like under conditions well-known in the art to derive the novel salts of the present invention; or (II) the crude 4-azo pyrazolidinedione compounds may be placed in a protic solvent, e.g., ethanol and hydrogenated in the presence of a catalyst. If the prospective product is poorly soluble in the protic solvent, 1 to 2 equivalents of, e.g., aqueous sodium hydroxide may be added prior to filtering off the catalyst; an additional amount of an aqueous acid may be added after removal of the catalyst to afford the salt, or the solution may be treated with the appropriate gas, e.g., hydrogen chloride to yield the novel salt when dried; or lastly, (III) the oxime intermediate synthesized by methods previously treated with this disclosure may be reduced to the amino compound in the presence of a protic solvent and the appropriate acid to yield the respective salt which is subsequently isolated.

A summary of the two principle methods of synthesizing the 4-hydroxy compounds of this invention, one of which is believed to be totally new to the art follows:

(I) condensation of the appropriate hydrazine with the appropriate oxy-substituted malonic acid or ester under conditions disclosed in the prior art provide novel 4-hydroxy developers. For example, K. M. Hammond, et al., Journal of the Chemical Society, 1062, (1957) teaches that condensation of dimethyl tetrahydropyranyloxymalonate, hereinafter referred to as an O-THP tartronate derivative, with hydrazobenzene in the presence of sodium ethoxide at 160°–170° C. gave 3:5-dioxo-1:2-diphenyl-4-tetrahydropyranyloxypyrazolidine. This was converted by p-toluenesulfonic acid present in a catalytic amount in ethanol at room temperature into 4-hydroxy-3:5-dioxo-1:2-diphenyl-pyrazolidine.

(II) Instead of employing an O-THP tartronate derivative, the novel method of obtaining the 4-hydroxy compounds of the present invention is to react the appropriate substituted hydrazine with a substituted malonic acid such as a benzyloxymalonic acid in the presence of an appropriate condensing agent such as DCC or EEDQ. On removal of the condensing agent, the crude 4-benzyloxy-3-hydroxy-5-pyrazolone is hydrogenated in the presence of a catalyst, e.g., 5–10% palladium on carbon under an initial pressure of about 15 to about 45 p.s.i. in order to cleave the benzyl group to give the 4-hydroxyl compound.

The 4-aminoalkyl and 4-aminoaryl compounds of the present invention, i.e., where X is NHR and R is alkyl or aryl, are readily synthesized by methods well-known in the art. For example, the prior art appreciates that such a substitution may readily be made by reacting the base compound with a malonic acid ester, such as N-benzyl-N-methyl-, N-benzyl-N-ethyl, or N-dimethylaminomalonate.

The following examples are illustrative of the preparation of compounds within the scope of the immediate invention and are not to be construed as limiting in any sense.

COMPOUND A

Preparation of:

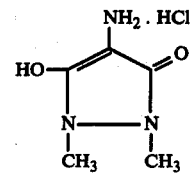

(1) Dimethylhydrazine (13.0 g., 0.216 M) and diethyl malonate (34.7 g., 0.216 M) were placed in a stainless steel pressure apparatus in the presence of absolute ethanol (80 ml.) for about 48 hours at 130° C. The apparatus was cooled in an ice bath and the ethanol stripped in vacuo to yield 28 grams of residue. The residue was triturated with isopropanol (50 ml.) and seeded with the authentic material. Crystallization began immediately afterwhich the mixture was stirred for about ½ hour. The product was filtered to give 3.8 g. of solid material. The filtrate was cooled and stirred for an additional 45 minutes in the presence of an ice bath in order to crystallize additional material (2.7 g.). The residue was sublimated to afford a further 1.7 g. of the crude material.

The total yield was 8.2 g. of the crude material having the formula:

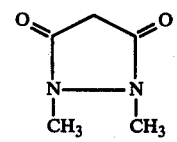

(2) 1,2-dimethylpyrazolidinedione obtained in step 1 (2.1g., 16.4 mmoles) was placed in 11.5 ml. of 90% acetic acid and cooled in an ice bath. A solution of sodium nitrite (1.19 g., 17.2 mmoles) in water (6.0 ml.) was added dropwise to the reaction mixture. The solution was then stirred for about 2 hours at below ambient temperature and the solution then further diluted with water. The red product was filtered, washed with water and air dried. The dry crude material (1.3 g., 7.4 mmoles) was recrystallized from water to yield 1.1 g. (6.3 mmoles) of material. The filtrates were combined, concentrated in vacuo, recrystallized from water and dried in vacuo to afford another 1.2 g. of the material having the formula:

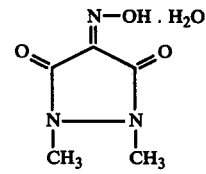

(3) 1,2-Dimethylpyrazolidinetrione-4-oxime hydrate (1.0 g., 5.7 mmoles) obtained in step 2 was combined with 10% palladium on carbon (0.5 g.) and ethanolic HCl (1.75 ml.) in methanol (about 25 ml.). After the theoretical amount of hydrogen was absorbed (theoretical uptake of $H_2$ was 11.4 mmoles), the hydrogenation was allowed to continue for another hour. The mixture was filtered through a celite pad and washed with methanol. No oxidation appeared to be taking place. The methanol was stripped from the filtrate to about 5 ml. at which point crystallization commenced.

The mixture which as crystallization began turned slightly yellow in color, was then diluted with diethyl ether and the product filtered. The filtrate was washed with diethyl ether and dried in a vacuum dessicator for about 16 hours.

1.0 (5.56 mmoles) of the title compound was obtained (melting range of 170° C.–172° C.).

COMPOUND B

Preparation of:

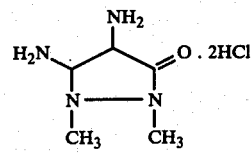

(1) A solution of 1,2-dimethylhydrazine (1.2 g., 20 mmoles) in absolute ethanol (5 ml.) was added to a solution of ethyl β-amino-β-ethoxyacrylate (3.18 g., 20 mmoles) in absolute ethanol (10 ml.). The resulting solution was stirred continuously for about 16 hours and then refluxed for 8 hours.

The ethanol was stripped in vacuo and the residue recrystallized from ethanol to afford a light yellow crystalline material (1.0 g.). The filtrate was stripped and the residue recrystallized from ethanol to afford another 200 mg. of the crude material.

The total yield was 1.2 g. of the crude material having the formula:

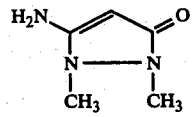

(2) An ice-cold solution of 3-amino-1,2-dimethyl-5-pyrazolone prepared according to the method of step 1 (4.45 g., 35 mmoles) in water (35 ml.) and concentrated hydrochloric acid (3.18 ml., 38.5 mmoles) was prepared. This solution was treated dropwise with a solution of sodium nitrite (2.42 g., 35 mmoles) in water (17 ml.). After the addition was complete, the red-orange mixture was stirred for an additional hour in the cold after which the solution was filtered. The product was washed with water and recrystallized from water to yield 4.8 grams of crude material. The filtrate was neutralized with sodium bicarbonate to afford additional crude material.

The total yield was 5.3 g. of the crude material having the formula:

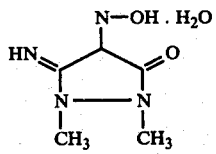

(3) 1,2-Dimethyl-pyrazolidinetrione-3-imide-4-oxime hydrate (2.2 g., 12.7 mmoles) obtained in step 2 was combined with 10% palladium on carbon (1.1 g.) and concentrated hydrochloric acid(2.1 ml.) in the presence of absolute methanol (250 ml.). After the theoretical amount of hydrogen was absorbed (25.4 mmoles) the mixture was filtered through a celite pad and the light yellow solution concentrated to about 100 ml. On cooling, the product precipitated from solution which product was then filtered and washed with cold methanol. The product was dried in vacuo to give 1.6 grams of the title compound as a beige crystalline solid (melting range 244° C.–246° C.).

The filtrate was treated with diethyl ether (about 200 ml.) and placed under refrigeration to precipitate a second quantity of the title compound (0.7 g.). This was recrystallized from methanol to afford a slightly yellow crystalline form of said compound (300 mg.).

COMPOUND C

Preparation of:

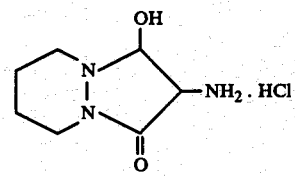

(1) The basic method of synthesis employed in steps 1 and 2 was that disclosed in *Chemical Abstract;* 56, 2460 (1962), and U.S. Pat. No. 2,841,584.

Butadiene (20.5 g., 0.38 M) and diethyl azodicarboxylate (66.1 g., 0.38 M) were placed in diethyl ether (200 ml.) and stirred at room temperature for 3½ days. The ethereal solution was shaken three times with equal amounts (100 ml. each) of a 10% solution of sodium bisulfite to reduce any starting azo compound present. The solution was then dried over magnesium sulfate and the ether stripped in vacuo to afford a crude yellow oil (78.2 g.). The oil was fractionated under reduced pressure (97°–100°/0.1 mm) to give 67.5 g. of material having the formula:

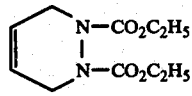

Diethyl 1,2,3,6-tetrahydropyridazine -1,2-dicarboxylate obtained in step 1 (20 g., 87.5 mmoles) was combined with absolute ethanol (150 ml.) and allowed to hydrogenate therein in the presence of platinum oxide (240 mg.). The uptake of hydrogen took place within an hour. The catalyst (platinum oxide) was filtered off and the ethanol thereafter stripped in vacuo to afford a crude oil (20 g.). This material was fractionated under reduced pressure (100°–104° C./0.1 mm) to yield 18.8 g. of material having the formula:

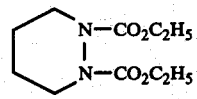

(3) The same procedure for synthesizing 3.6-dimethylhexahydropyridazine disclosed in the *Journal of the American Chemical Society,* 84 590 (1962) was employed in the synthesis of the unsubstituted hexahydropyridazine.

Diethyl hexahydropyridazine-1,2-di-carboxylate, (18.8 g., 81.0 mmoles) the hydrogenated product obtained in step 2 was heated at reflux under an atmosphere of nitrogen in a solution of potassium hydroxide (18.2 g., 0.32 M) in methanol (35 ml.) for 24 hours. The mixture was concentrated after filtering off the potassium carbonate and extracting the residue with diethyl ether. The solvent was then removed under reduced pressure (65°/100mm). The oil was taken up in diethyl ether (about 60 ml.), filtered to remove any excess potassium hydroxide and dried over anhydrous sodium sulfate. The diethyl ether was then stripped in vacuo to afford an oil which was fractionated under reduced pressure to yield 3.9 g. (56% yield) of a crude material having the formula:

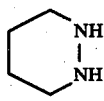

(4) Hexahydropyridazine (38 g., 44.2 mmoles) prepared according to the method of step 3 in absolute ethanol (15 ml.) was added to ethyl β-amino-β-ethoxyacrylate (7.02 g., 44.2 mmoles) in ethanol (25 ml.). The reaction mixture was stirred at room temperature for 3½ days. The mixture was thereafter heated on a steam bath for approximately 1 hour and then cooled in an ice bath to precipitate 2.8 grams (41% yield) of a white product (melting range of 233° C.–236° C.).

The filtrate was concentrated to insipient crystallization and cooled to afford a second crop (900 mg.) having a light yellow color (melting range of about 233° C.–236° C.).

To the resulting filtrate (approximately 30 ml.) was added diethylether (30 ml.) in order to precipitate 400 mg of a third product (melting range of 227° C.–232° C.).

The total yield was 4.1 grams or a 60% yield of the material having the formula:

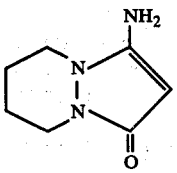

(5) The basic method of synthesis employed in this step was disclosed in Helvetica Chimica Acta, 33, 1190 (1950).

3-Amino-1,2-tetramethylene-5-pyrazolone (2.8 g., 18.2 mmoles) obtained in step 4 was combined with 2N sulfuric acid (18.2 ml.) and the solution heated at reflux for 1 hour. After the mixture was allowed to cool to room temperature, sodium bicarbonate (1.53 g., 18.2 mmoles) was added to the mixture and the same stirred for about 0.5 hours. The mixture was then stripped in vacuo and the residue extracted with hot isopropanol (50 ml.), filtered and concentrated in vacuo.

The yellow solution was cooled in an ice bath and seeded with authentic diketo compound to precipitate the product. This product was filtered, washed with a small amount of cold isopropanol and then air dried to afford 1.74 grams (11.3 mmoles or a 62% yield) of the crude material (melting range of 117° C.–119° C.).

The filtrate was concentrated and cooled to afford 0.27 additional grams of the crude material (melting range 116° C.–119° C.).

The total yield was 2.01 g. (72%) of the compound having the formula:

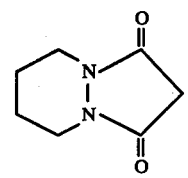

(5a) An alternate method of synthesizing 1,2-tetramethylene pyrazolidinedione was to form a mixture of the hexahydropyridazine (1.0 g., 11.6 mmoles) and malonic acid (1.21 g., 11.6 mmoles) in dry dioxane (50 ml.). To this solution was added N,N'-dicyclohexyl-carbodiimide (5.26 g., 25.5 mmoles) in one portion. The reaction mixture immediately precipitated N,N'-dicyclohexylurea. The mixture was allowed to stir at room temperature for 2 hours after which it was filtered to remove the N,N'-dicyclohexylurea and washed with dioxane. The filtrate was stripped to dryness and the residue recrystallized from isopropanol to yield 900 mg. (50%) of material (melting range of 117° C.–120° C.).

(6) Regardless of which method of obtaining 1,2-tetramethylenepyrazolidinedione was employed, this compound (1.54 g., 10 mmoles) was combined with 90% acetic acid (7.5 ml.) and an ice-cold solution of the same prepared by cooling in an ice bath. To this solution was added a solution of sodium nitrite (725 mg.; 10.5 mmoles) in water (5 ml.). The red mixture was allowed to stir in the cold for 1 hour, after which it was diluted with water (12 ml.) and again stirred in the cold for an additional 1 hour. The product was filtered and allowed to air dry. The filtrate was then stripped in vacuo and the residual oil treated with water. The crystalline material was filtered off, combined with the previously air-dried material and both recrystallized from water to yield 1.2 g. (60%) of material (melting range of 234° C.–236° C.) the final product having the formula:

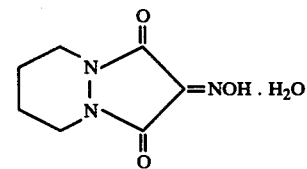

(7) 1,2-tetramethylene pyrazolidinetrione-4-oxime hydrate (1.0 g., 4.98 mmoles) obtained in step 6 was combined with 10% palladium on carbon (0.5 g.), methanol (25 ml.) and concentrated hydrochloric acid (0.5 ml.). After the theoretical amount of hydrogen was absorbed, the methanol was stripped from the hydrogenation mixture to a volume of about 10 ml. and the mixture cooled in a dry-ice acetone bath in order to precipitate the product. The product was filtered, washed with cold methanol and dried in vacuo. The isolated title compound (0.87 g., 85% yield) was a light yellow hygroscopic crystalline solid (melting range of 118° C.–120° C.).

COMPOUND D

Preparation of

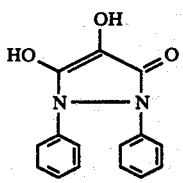

The *Journal of the Chemical Society*, 1957, 1065 disclosed the title compound as a reducing agent and the synthetic techniques disclosed in the reference were repeated as follows:

(1) Sodium (0.92 g., 40 mmoles) was dissolved in absolute ethanol (150 ml.). Hydrazobenzene (7.36 g., 40 mmoles) and diethyl tetrahydropyranyloxymalonate (10.4 g., 40 mmoles) were added to the sodium/ethanol solution and the entire reaction mixture heated at reflux for 1 hour. The ethanol was distilled off and the residue heated at 175° C.-200° C. under vacuum for 2 hours.

The residue, after cooling, was dissolved in water (100 ml.) and diethyl ether (100 ml.). The aqueous layer was re-extracted with diethyl ether twice (100 ml. each instance) and then cooled in an ice bath. The cooled aqueous layer was then acidified with acetic acid (3.0 g., 50 mmoles). A gummy precipitate separated which was taken up in chloroform twice (100 ml. ea.) and dried over sodium sulfate. The chloroform was stripped in vacuo to afford a dark oil (10.9 g.) which was employed in the following step without further purification. This crude material is represented by the formula:

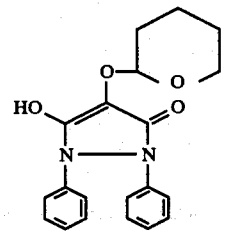

(2) The crude THP derivative obtained in step 1, i.e., 1,2-diphenyl-3-hydroxy-4-tetrahydropyranyloxy-5-pyrazolone (10.9 g., 31 mmoles) was dissolved in absolute ethanol (250 ml.). To this solution was added para-toluenesulfonic acid (0.2 g.) as a catalyst which was dissolved and the solution thereafter stirred for several days.

No product came out of solution. The mixture was concentrated in vacuo to about 100 ml. An aliquot was cooled in dry-ice acetone and scratched to produce a white crystalline material. The balance of the concentrated material was cooled in an ice bath and seeded after which it was stirred in the cold for about 1 hour. The material was then filtered and washed with cold ethanol. One gram (1.0 g.) of the ethanol solrate (melting range of 201° C.-203° C.), was dried for 1 hour at 100° C. to desolvate the material. The filtrate was placed in a freezer for about 16 hours to afford a second sample of the title compound.

Diethyl tetrahydropyranyloxymalonate

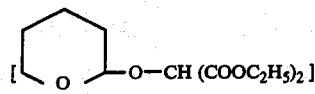

used in step (1) was prepared for the dimethyl ester (dimethyl tetrahydropyran-2-yloxymalonate) discussed in the *Journal of the Chemical Society*, 2130 (1956).

COMPOUND E

Preparation of:

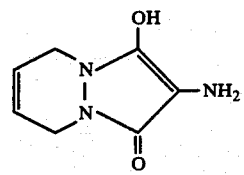

(1) Compt. Rend. 236. 1365 (1953) disclosed the synethesis techniques employed in the immediate reaction sequence for obtention of the subject hydrazine.

A solution of diethyl 1,2,3,6-tetrahydropyridazine-1,2-dicarboxylate (22.8 g., 0.1 M) and potassium hydroxide (25.2 g., 0.45 M) in methanol (100 ml.) was heated at reflux for 20 hours. The potassium carbonate was filtered off, washed with diethyl ether and the solvent stripped in vacuo. The residue was treated with diethyl ether (100 ml.), filtered, and the ether thereafter distilled while the residue was distilled under reduced pressure (80° C.-84° C./20 mm). The fraction was collected and possessed the formula:

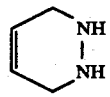

(2) The basic procedure for the synthesis of hexahydropyridazine disclosed in the preparation of compound C, step 4 was employed in the immediate reaction sequence.

1,2,3,6-Tetrahydropyridazine (2.44 g., 29 mmoles) obtained in step 1 was added to a solution of ethyl β-amino-β-ethoxyacrylate (5.0 g., 29 mmoles) in ethanol (10 ml.). The mixture was stirred at room temperature continuously for about 16 hours and then heated at reflux for 1 hour. The mixture was then cooled in an ice bath to precipitate the product. The product was filtered, washed with cold ethanol and air dried to afford 2.0 grams (46% yield) of the crude material. The filtrate was concentrated in vacuo and cooled in an ice bath to afford an additional 1.0 gram (23% yield) of this slightly yellow crystalline solid (melting range of 225° C.-227° C.) having the formula:

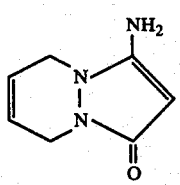

(3) The procedure for the synthesis of the hexahydropyridazine derivative disclosed in the synthesis of Compound C, step 5 was employed in the immediate reaction sequence.

The compound obtained in step 2 (2.0 g., 13.3 mm) and identified by the immediately preceeding formula was heated at reflux in 2N sulfuric acid 13.3 ml. for about 1 hour. The mixture was thereafter cooled in an ice bath and treated with sodium bicarbonate (1.12 g., 13.3 mmoles). The water was stripped in vacuo and the residue dried in a vacuum dessicator for about 16 hours. The residue was extracted with hot isopropanol (20 ml.), filtered to remove the inorganic salts and stripped in vacuo.

The residue was recrystallized from isopropanol to afford a material (melting range of 136° C.-138° C.) having the formula:

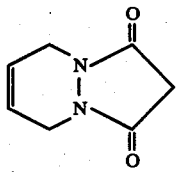

(3a) An alternate way of obtaining the compound of the immediately-preceeding formula was accomplished by preparing a solution of 1,2,3,6-tetrahydropyridazine (11.3 g., 0.135 M) in dry dioxane (500 ml.). To this solution was added malonic acid (14.0 g., 0.135 M) resulting in precipitation of the salt. N-N'-dicyclohexylcarbodiimide (59. g., 0.296 M) was added in one portion and the resulting mixture allowed to stir at room temperature for about 24 hours.

The N-N'-dicyclohexylurea was filtered off and washed with dioxane. The filtrate was stripped to dryness in vacuo and recrystallized from isopropanol (100 ml.) to afford 5.8 grams of crude material (melting range of 135° C.-137° C.).

(4) Whether prepared by the method of step 3 or 3a, the compound of the immediately preceeding formula (1.83 g., 12 mmoles) was placed in 90% acetic acid (8 ml.) and the solution cooled in an ice bath. The mixture was then treated with sodium nitrite (870 mg., 12.6 mmoles) in water (5.0 ml.) and the mixture stirred in the cold for 1.5 hours. The mixture was then diluted with water (25 ml.) and the product filtered, washed with cold water and air dried for approximately 16 hours to afford 1.8 grams (75% yield) of a red-orange crystalline solid (melting range of 222° C.-224° C.). The filtrate was stripped to dryness and the residue recrystallized from water to afford a second sample of the crude material (150 mg.) giving a total yield of 1.95 g. (82% yield) of material having the formula:

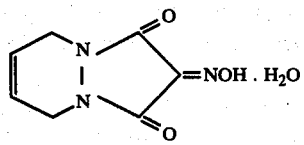

(6) The above-identified material (1.72 g., 8.64 mmoles) obtained in step 4 was suspended in water (18 ml.) and under an atmosphere of argon treated with sodium dithionite (4.0 g., 23 mmoles). The red color of the oxime discharged to produce a white precipitate. The mixture was stirred for about 1 hour, filtered argon and washed with cold water. It was then dried in vacuo to afford 1 gram (70% yield) of the title compound as a slightly yellow crystalline solid (melting range of 262° C.-265° C.).

Four hundred milligrams (400 mg.) of this material was recrystallized from hot water to afford a second and more nearly pure sample of the title compound (175 mg.) as a beige crystalline solid.

COMPOUND F

Preparation of:

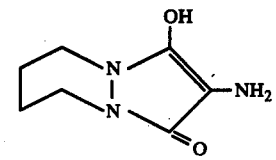

The synthesis techniques employed in the preparation of the immediate bicyclic hydrazine were disclosed in *Tetrahedron Letters*, 1973 No. 30, pp. 2859-2862.

Cyclopentadiene (36.3 g., 0.55 M) was slowly added to a solution of dibenzyl azodicarboxylate (149 g., 0.5 M) in diethyl ether (650 ml.) at about 10° C. The resulting mixture was alllowed to warm to room temperature and was stirred for about 16 hours.

Within the first hour after addition of the cyclopentadiene a white crystalline substance commenced to precipitate from the solution. After 16 hours later the white solid was filtered off, washed with diethyl ether and air dried to afford 120.4 g. of crude material (melting range of 68° C.-70° C.).

The filtrate was concentrated to about 200 ml. and placed in a freezer (−25° C.) to afford an additional 50.1 g. of material having the formula:

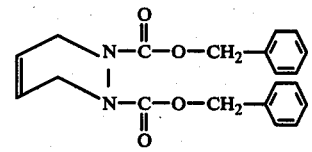

(2) Dibenzyl 2,3-diazobicyclo[2.2.1]-5-heptene-2,3-dicarboxylate (40.0 g., 0.11 M) obtained in step 1 was placed in methanol (200 ml.) and hydrogenated at an initial pressure of 45 p.s.i. in the presence of 5% palladium on carbon (1.0 g.). After about 5 hours the theoretical uptake of hydrogen ceased and the mixture was filtered. The methanol was stripped in vacuo and the product used without further purification in step 3 which product possessed the formula:

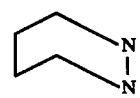

(3) 2,3-Diazobicyclo[2.2.1]-heptane (10.8 g., 0.11 M) obtained in step 2 and malonic acid (11.5 g., 0.11 M) were placed in dioxane (400 ml.) and the resultant mixture treated with N,N'-dicyclohexylcarbodiimide (50 g., 0.24 M). The mixture was stirred for about 16 continuous hours after which the N,N'-dicyclohexylurea was filtered off and the dioxane stripped in vacuo to afford an oil substance. Attempts to recrystallize this oil from ethanol or isopropanol failed. The crude oil material was used in the ensuing steps without additional purification which material possessed the formula:

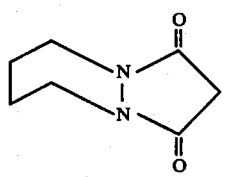

(4) A mixture of the crude material obtained in step 3 (10.8 g., 65 mmoles) in ice cold water (100 ml.) was added to concentrated hydrochloric acid (5.37 ml., 65 mmoles). To this cold mixture was added dropwise sodium nitrite (4.5 g., 65 mmoles) in water (20 ml.). After addition, the mixture was stirred for an additional hour in the cold environment. No precipitation of the product occurred. The mixture was filtered to remove the gummy material and the water stripped therefrom in vacuo. The crude red material was used without further purification and possessed the formula:

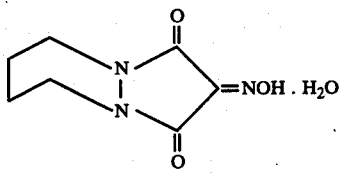

(5) A mixture of the crude material (65 mmoles) obtained in step 4 in water (50 ml.) was treated with sodium dithionite (23 g., 130 mmoles) and the mixture allowed to stir for about 16 hours at room temperature. The resultant white crystalline material was filtered, washed with water and dried in vacuo over phosphorus pentoxide to yield the title compound.

COMPOUND G

Preparation of:

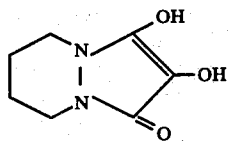

(1) Diethyl benzyloxymalonate was prepared according to the procedure disclosed in the *Journal of the Chemical Society*, 1065, (1957).

Diethyl benzyloxymalonate (6.0 g., 22.6 mmoles) was added to an ice cold solution of potassium hydroxide (2.66 g., 47.5 mmoles) in absolute ethanol. The mixture was stirred until a homogenous mixture was obtained and stirring continued for an additional 30 minutes in a cold environment. Stirring was thereafter conducted under an atmosphere of argon at room temperature for about 16 hours. The product was filtered, washed with ethanol, and diethyl ether and then dried under vacuum to yield the dipotassium salt of benzyloxymalonic acid (4.4 g., 15.4 mmoles, 68% yield).

An additional amount of dipotassium salt was prepared to afford 6.0 g. (21 mmoles) of the same which was placed in water (6 ml.) and cooled in an ice bath. The mixture was then treated with concentrated hydrochloric acid (3.48 ml., 42 mmoles) after which the mixture was stripped in vacuo and the residue thoroughly dried in a vacuum dessicator for about 16 hours to afford potassium chloride, water and benzyloxymalonic acid having the formula:

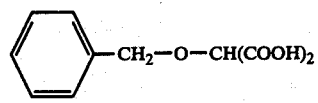

No effort was made to remove the potassium chloride since it was felt that the presence of this salt should not interfere in the following cyclization step.

(2) More benzyloxymalonic acid was synthesized so that a mixture of the same (6.7 g. of benzyloxymalonic acid + 2KCl $H_2O$ molecular weight about 377.31) and hexahydropyrazolidine (1.55 g., 18 mmoles) was prepared to which was added N,N'-dicyclohexylcarbodiimide (8.25 g., 40 mmoles). The mixture was stirred at room temperature for about 64 hours after which time the N,N'-dicyclohexylurea was filtered off and washed with diethyl ether. The filtrate was stripped in vacuo and the residue taken up in ethyl acetate (50 ml. each extraction). The bicarbonate extracts were combined, cooled and acidified with concentrated hydrochloric acid (about 12.4 ml.). The mixture was then extracted three times with chloroform (50 ml. each extraction), and the chloroform stripped in vacuo to afford 2.4 g. of crude material which was reduced in step 3 without further purification, said crude material having the formula:

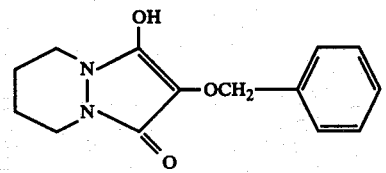

(3) The crude 1,2-tetramethylene-4-benzyloxy-3-hydroxy-5-pyrazolone (2.4 g.) obtained in step 2 was placed in absolute ethanol (50 ml.) and hydrogenated in the presence of 5% palladium on carbon (0.5 g.) under an initial pressure of 41 p.s.i. for about 16 hours. The catalyst was filtered through a celite pad and the filtrate stripped in vacuo to afford 1.7 grams of a crude material.

This material was taken up in hot isopropanol, cooled in a dry-ice acetone, scratched and warmed to room temperature. The mixture was again cooled to induce crystallization from the isopropanol to afford 700 mg. of the title compound solvate in isopropanol.

The title compound was heated in a vacuum oven at 100° C. for about 1 hour to remove the isopropanol.

COMPOUND H

Preparation of:

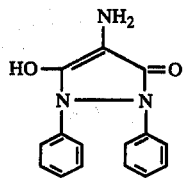

(1) Ber., 73, 820 (1940) disclosed the synthesis techniques employed in the immediate reaction sequence for reaction of a hydrazine with a sodium salt of diethylmalonate.

A solution of sodium ethoxide was prepared by adding sodium (12.5 g., 0.543 mmoles) in absolute ethanol (400 ml.). 1,2-Diphenylhydrazine (100 g., 0.543 mmoles) and diethyl malonate (87 g., 0.543 M) were added to the sodium ethoxide solution in 1 portion. The resulting mixture was heated to reflux for 1.5 hours after which the ethanol was distilled off at atmospheric pressure and collected (about 150 ml.). The balance of the ethanol was removed under reduced pressure (about 100 mm). The resulting reddish solid was heated in an oil bath at about 220° C. while under reduced pressure. When the temperature of the residue reached 200° C., heating was continued for an additional 0.5 hour after which the residue was allowed to cool for about 16 hours.

The residue was then treated with water (550 ml.) and stirred to dissolve the sodium salt of the pyrazolidinedione. The mixture was twice extracted with diethyl ether (500 ml. each instance) and the aqueous solution neutralized with concentrated hydrochloric acid to precipitate the product. The crude material was recrystallized from ethanol to afford 59 g. (0.234 M; 45% yield) of the material (melting range of 176° C.-178° C.) possessing the formula:

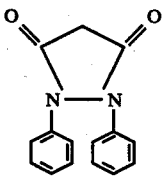

The basic synthesis techniques employed in steps (2) and (3) of the immediate reaction sequence were disclosed in the *Journal of Chemical Society*, 1066, (1957).

(2) A solution of benzenediazonium chloride was prepared as follows: To an ice cold (about 5° C.) solution of aniline hydrochloride (3.24 g., 25 mmoles) in water (10 ml.) and concentrated hydrochloric acid (2.1 ml., 25 mmoles) was added dropwise with stirring a solution of sodium nitrite (1.9 g., 27.5 mmoles) in water (10 ml.). After addition the solution was stirred in the cold for an additional 15 minutes.

To an ice cold (about 5° C.) suspension of the compound obtained in step 1 (6.3 g., 25 mmoles) and sodium acetate (10.3 g., 125 M) in water (125 ml.) and chloroform (60 ml.) was added the benzenediazonium chloride solution (25 mmoles) prepared above. When addition was complete, the mixture was allowed to stir in the cold for another 2 hours. The chloroform layer was separated and the aqueous layer extracted with chloroform (about 50 ml.). The combined chloroform extracts were dried over anhydrous sodium sulfate. The chloroform was stripped in vacuo to afford an oil which crystallized on cooling. The crude mixture was recrystallized from ethanol to yield 7.1 g. (20 mmoles) of a crude material (melting range of 183° C.-185° C.). The mother liquor was placed under refrigeration for about 16 hours to afford an additional 0.8 grams of the material having the formula:

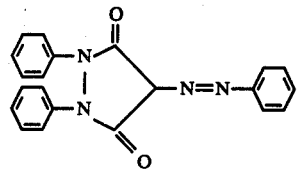

(3) The material (3.5 g., 10 mmoles) obtained in step 2 was placed in absolute ethanol (60 ml.) and hydrogenated at about 35 p.s.i. in the presence of 10% palladium on carbon (1.5 g.). After the theoretical amount of hydrogen had been absorbed, the mixture was shaken for another 30 minutes. The mixture was then stirred with 1N sodium hydroxide (10 ml.) under an atmosphere of nitrogen for 1.5 hours and thereafter filtered through a celite pad. The filtrate was neutralized with 6N hydrochloric acid (1.66 ml.) to precipitate 1.8 grams (65 mmoles, 65% yield) of the title compound (melting range of 235° C.-237° C.).

COMPOUND I

Preparation of:

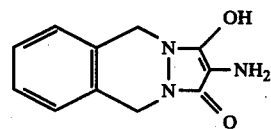

(1) Ber. 26, 2210 (1893) and *Journal of the Chemical Society*, 659 (1943) "1:2:3:4-Tetrahydrophthalazine Hydrochloride" disclosed the basic synthesis techniques used in the preparation of the compound of step (1).

A mixture of phthalazine (14.3 g., 0.11M) in water (350 ml.) and concentrated hydrochloric acid (9.1 ml., 0.11 M) was treated with 7% sodium amalgam (184 g.) during a 1 hour period. After addition was complete the mixture was allowed to stir for an additional 2 hours. The aqueous layer was decanted from the mercury and made strongly alkaline (about pH 14) with a 50% solution of potassium hydroxide. The mixture was then extracted six times with chloroform (100 ml. each instance) and then dried over sodium sulfate. The dry chloroform solution was treated with anhydrous hydrogen chloride to afford the salt (12.1 g., 0.07 M). About one third of this material was converted to free base, continuously extracted with chloroform for about 16 hours, and dried over sodium sulfate. The crude material was then stripped to afford 5.3 g. (39.6 mmoles) of material having the formula:

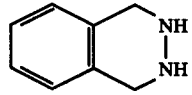

(2) A mixture of the material (5.3 g., 39.6 mmoles) obtained in step 1 and malonic acid (4.3 g., 41 mmoles) in dioxane (150 ml.) was prepared, to which was added N,N'-dicyclohexylcarbodiimide (18.5 g., 90 mmoles). The mixture was allowed to stir for about 4 hours at room temperature. The N,N'-dicyclohexylurea was filtered off, washed with dioxane and the filtrate stripped in vacuo to dryness (about 11 g.). The crude material was taken up in ethyl acetate (about 125 ml.) and thereafter extracted with 1N potassium bicarbonate solution in four portions (400 ml., 100 ml. each). The aqueous extracts were combined and acidified with concentrated hydrochloric acid (about 35 ml.). The mixture was then re-extracted with ethyl acetate in three portions (300 ml., 100 ml. each). The ethyl acetate extracts were then dried over magnesium sulfate and stripped in vacuo to afford 6.0 grams of a tacky solid.

The solid material was recrystallized from ethanol treated with carbon and allowed to cool slowly to yield 2.9 grams (35% yield) of material (melting range of 158° C.–161° C.). The filtrate was concentrated and placed in a refrigerator for approximately 16 hours to yield an additional 400 mg. of the material having the formula:

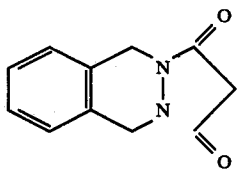

(3) An ice-cold solution of the material obtained in step 2 was prepared by placing said material (2.0 g., 9.9 mmoles) in 90% acetic acid (15 ml.). To this solution was added dropwise sodium nitrite (71.8 mg., 10.4 mmoles) in water (6 ml.). After addition was complete, the red mixture was allowed to stir in the cold for 2 additional hours, after which the mixture was diluted with cold water (about 25 ml.) and filtered. The material was air dried to yield 2.0 grams (81% yield) of material (melting range in water of 212° C.–215° C.) possessing the formula:

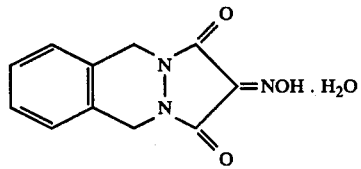

(4) The compound obtained in step (1.0 g., 4.02 mmoles) was suspended in water (20 ml.) to which mixture was added in one portion, sodium dithionite (2.8 g., 16.1 mmoles). The mixture was allowed to stir at room temperature for 2 hours after which it was cooled and then filtered. The resultant residue was washed with cold water and dried in vacuo to yield 850 mg. (98% yield) of the title compound (melting range of 260° C.–263° C.).

COMPOUND J

Preparation of:

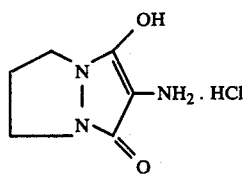

(1) The basic synthetic techniques employed in step 1 were those disclosed in the *Journal of the American Chemical Society*, 65, 29 (1943) for preparation of the specific pyrazolidine.

1,3-Dibromopropane (404 g., 2.0 mmoles) was added to a refluxing solution of hydrazine hydrate (200 grams; 4.0 mmoles) in ethanol (800 ml) over a 2.5 hour period. After addition was complete, the reaction mixture was heated for an additional hour and thereafter cooled to about 0° C.–5° C. The precipitated salt ($N_4H_4 \cdot HBr$) was filtered off and the filtrate treated with potassium hydroxide (100 grams; 1.8 M) to make the solution alkaline. The potassium bromide was filtered off and the ethanol stripped in vacuo.

The residue was distilled under reduced pressure (26 mm) and the fraction (boiling at 35° C.–85° C./26 mm) was also collected, then stirred with barium oxide for an additional 0.5 hours and thereafter redistilled at atmospheric pressure under argon. A third fraction (boiling at 133° C.–148° C.) was collected giving a total yield of 13.5 grams (9.4% yield) of the crude material having the formula:

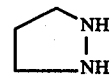

(2) Hexahydropyridazine (12.5 g. 0.174 M) obtained in step 1 was added to a mixture of ethyl- -aminoethoxyalkylate (27.6 g., 0.174 M) in absolute ethanol (60 ml.). The reaction mixture was stirred at room temperature for about 6 hours and then heated at reflux overnight (about 16 hours). A precipitate was noted at the completion of the 16 hour period after which time the mixture was cooled in an ice bath to yield a total of 12.6 grams (62% yield) of crude material. The filtrate was concentrated in vacuo and cooled in an ice bath to afford a second sample of the same material (melting range of 235° C.–238° C.) having the formula:

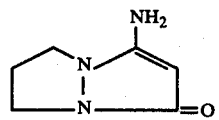

(3) A solution of 3-amino-1,2-tetramethylene-5-pyrazolone (2.0 g., 14.4 mm) obtained in step 2 in 2N sulfuric acid (14.4 ml) was heated at reflux for about 1 hour. The solution was thereafter cooled to ambient temperature and then treated with sodium bicarbonate (1.21 g., 14.4 mm). After stirring for about 30 minutes, the water was stripped in vacuo and dried in vacuo over phosphorous pentoxide overnight (about 16 hours). The residue was then extracted with hot ethanol and filtered to remove the salts. The filtrate was concentrated to about one half its original volume resulting in a light yellow-colored mixture which was cooled in an ice bath and seeded with a chromatographically pure sample to yield about 100 mg. of the material having the formula:

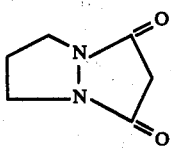

(4) Benzenediazonium chloride was synthesized by first preparing a solution of sodium nitrite (1.05 g., 15.2 mmoles) in water (6.0 ml). This first solution was added dropwise to a second solution (ice cold) of aniline hydrochloride (1.88 g., 14.5 mmoles), concentrated hydrochloric acid (1.2 ml., 14.5 mmoles) and water (6.0 ml). After addition, the mixture was allowed to stir in the cold for about 15 minutes and used directly.

The resultant diazonium salt solution was added dropwise to a mechanically-stirred ice-cold mixture of the crude material (2.00 g., 14.5 mmoles) prepared as in step 3, sodium hydroacetate (9.75 g., 71.5 mmoles) in water (72 ml), and chloroform (35 ml). After addition, the mixture was stirred in the cold for about 2 hours. The chloroform layer was then separated and the aqueous layer extracted with chloroform (50 ml). The combined extracts were dried over sodium sulfate and the chloroform stripped in vacuo to afford the crude azo compound having the formula:

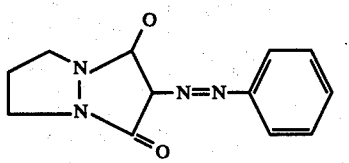

(5) The azo compound (400 mg.; 1.65 mmoles) obtained in step 4 was placed in absolute ethanol (20 ml) and hydrogenated in the presence of 10% palladium on carbon (about 200 mg.).

After the theoretical amount of hydrogen was absorbed, the reaction mixture was filtered through a celite pad and washed with ethanol. The filtrate was stripped to dryness in vacuo and the red-orange residue triturated with chloroform to remove the oxidation products. The remaining residue was dissolved in methanol, cooled and treated with hydrogen chloride gas. The mixture was thereafter placed in the freezer (above -20° C.) affording the title compound as a tacky crystalline product having the formula:

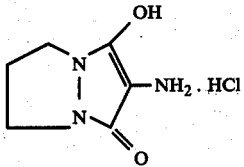

It will be appreciated that other compounds within the scope of the present invention may be prepared according to the foregoing procedures.

As mentioned previously, the compounds of the present invention as represented in formula I are useful as photographic developing agents. While all of the 3:5-pyrazolidines synthesized were evaluated for reducing agent properties and proved to be effective silver halide reducing agents, the degree of their effectiveness varied from compound to compound. Thus, some of these 3:5-pyrazolidines are desirably employed in conventional or "tray" development while others find added utility in, for example, diffusion transfer processes for forming images in silver or in color. Such processes are now well known in the art; see for example, U.S. Pat. Nos. 2,543,181; 2,647,056; 2,983,606; 3,719,489; etc. In processes of this type, an exposed silver halide emulsion is treated with a processing composition whereby the exposed silver halide emulsion is developed and an imagewise distribution of diffusible image-forming components is formed in the unexposed and undeveloped portions of the silver halide emulsion. This distribution of image-forming components is transferred by imbibition to an image-receiving stratum in superposed relationship with the silver halide emulsion to provide the desired transfer image.

In silver diffusion transfer processes, processing of the exposed silver halide emulsion is effected in the presence of a silver halide solvent, such a sodium thiosulfate or uracil, which forms a diffusible complex with the undeveloped silver halide. The soluble silver complex thus formed diffuses to the superposed image-receiving layer where the transferred silver ions are deposited as metallic silver to provide the silver transfer image.

In preparing silver prints in this manner, the image-receiving layer preferably includes certain materials, the presence of which, during the transfer process has a desirable effect on the amount and character of silver precipitated on the image-receiving element. Materials of this type are specifically described in U.S. Pat. Nos. 2,690,237 and 2,698,245, both issued in the name of Edwin H. Land on Dec. 28, 1954 and U.S. Pat. No. 3,671,241 of Edwin H. Land issued on June 20, 1972.

The photosensitive element may be any of those conventionally used in silver diffusion transfer processes and generally comprises a silver halide emulsion carried on a base, e.g., glass, paper or plastic film. The silver halide may be a silver chloride, iodide, bromide, iodobromide, chlorobromide, etc. The binder for the halide, though usually gelatin, may be a synthetic polymer such as polyvinyl alcohol, polyvinyl pyrrolidone and their copolymers.

Separating the photosensitive element from the image-receiving layer may be controlled so that the layer of processing composition is removed from the image-receiving layer or the layer of processing composition is caused to remain in contact with the image-receiving layer, e.g., to provide it with a protective coating. Techniques which enable such results to be accomplished as desired are described in U.S. Pat. No. 2,647,054 issued to Edwin H. Land on July 28, 1953. In general, the processing reagents are selected so that traces remaining after the solidified processing layer has been separated from the silver image or which remain in said layer adhered as a protective coating on the silver image are colorless or pale, so as not to appreciably affect the appearance of the image and to have little or no tendency to adversely react with the silver image.

Some of the developing agents of the present invention, due to their nearly colorless oxidation product comprise a particularly useful group of developers for diffusion transfer processes wherein there is employed a positive transfer image and a negative silver image, the two images being in separate layers on a common, transparent support and viewed as a single, positive image. Such positive images may be referred to for convenience as "integral positive-negative transparencies".

Examples of film units which provide such integral positive-negative transparencies are set forth, for example, in U.S. Pat. Nos. 3,536,488; 3,894,871; 3,615,426; 3,615,427; 3,615,428 and 3,615,429. Moreover, the preferred compounds of this invention, namely, again due their nearly colorless oxidation product, are useful in the production of silver transfer images where it is inconvenient or undesired to wash the silver image after separation of the negative and positive elements.

Some of the subject developing agents also may be employed in diffusion transfer processes where the final image is in dye, and as appropriate for the particular color process, the developing agent may be used as the principal developer, for example, in the processes of aforementioned U.S. Pat. No. 3,719,489 or as an auxiliary developer, for example, in the processes of aforementioned U.S. Pat. No. 2,983,606. In these diffusion transfer processes, a photosensitive component comprising at least one photosensitive silver halide emulsion having a dye image-providing compound associated therewith in the same or in an adjacent layer is exposed to form a developable image and then developed with a processing composition to form an imagewise distribution of a soluble and diffusible image-providing material is transferred, at least in part, by diffusion, to a superposed image-receiving component comprising at least a dyeable stratum. These processes rely for color image formation upon a differential in mobility or solubility of dye image-providing material obtained as a function of development so as to provide an imagewise distribution of such material which is more diffusible and which, therefore, may be selectively transferred to the superposed dyeable stratum. The differential in mobility or solubility may be obtained, for example, by a chemical action such as a redox reaction, a silver ion-assisted cleavage reaction or a coupling reaction.

The dye image-providing materials which may be employed in such processes generally may be characterized as either (1) initially soluble or diffusible in the processing composition but which are selectively rendered non-diffusible in an imagewise pattern as a function of development; or (2) initially insoluble or non-diffusible in the processing composition but which are selectively rendered diffusible in an imagewise pattern as a function of development. These materials may be complete dyes or dye intermediates, e.g., color couplers.

Examples of initially soluble or diffusible materials and their use in color diffusion transfer processes are disclosed, for example, in U.S. Pat. Nos. 3,087,817; 2,661,293; 2,693,244; 2,698,798; 2,802,735; and 2,983,606. Examples of initially non-diffusible materials and their use in color transfer systems are disclosed in U.S. Pat. Nos. 3,443,939; 3,443,940; 3,227,550; 3,227,551; 3,227,552; 3,227,554; 3,243,294; 3,445,228; 3,719,488; and 3,719,489.

In any of these systems, multicolor images may be obtained by employing a photosensitive element containing at least two selectively sensitized silver halide layers each having associated therewith a dye image-providing material exhibiting the desired spectral absorption characteristics. The most commonly employed elements of this type are the so-called tripack structures employing a blue-, a green- and a red-sensitive silver halide layer having associated therewith, respectively, a yellow, a magenta and a cyan image-providing material.

The photosensitive and image-receiving elements may be separate components which are brought together during processing and thereafter retained together as the final print or separated following image formation; or they may together comprise a unitary structure, e.g., an integral negative-positive film structure wherein the negative and positive, i.e., photosensitive element and image-receiving element are laminated and/or otherwise physically retained together at least prior to image formation.

Integral negative-positive film structures adapted for forming color transfer images viewable without separation, i.e., wherein the image-receiving component containing the dye transfer image need not be separated from the photosensitive component for viewing purposes are described and claimed in U.S. Pat. Nos. 3,415,644; 3,415,645; 3,415,646; 3,573,043; and 3,573,044 in the name of Edwin H. Land and in U.S. Pat. Nos. 3,594,164 and 3,594,165 in the name of Howard G. Rogers.

In conventional development and in diffusion transfer photographic processes, the subject compounds may be used as the sole silver halide developing agent, or they may be employed in combination with another halide developing agent as an auxiliary developer or as the main component of the developing combination. Examples of developing agents that may be used in combination with the subject compounds include hydroquinone and substituted hydroquinones, such as, tertiary butyl hydroquinone, 2,5-dimethyl hydroquinone, methoxyhydroquinone, ethoxyhydroquinone, chlorohydroquinone; pyrogallol and catechols, such as, cathechol, 4-phenyl catechol and tertiary butyl catechol; aminophenols, such as, 2,4,6-triaminophenol, 2,4-diaminophenol dihydrochloride and 4,6-diamino-ortho-cresol; 1,4-diaminobenzenes, such as, p-phenylenediamine, 1,2,4-triaminobenzene and 4-amino-2-methyl-N,N-diethylaniline; ascorbic acid and its derivatives, such as, ascorbic acid, isoascorbic acid and 5,6-isopropylidine ascorbic acid; and hydroxylamines, such as N,N-di-(2-ethoxyethyl) hydroxylamine and N,N-di-(2-methoxyethoxyethyl) hydroxylamine.

When the appropriate compounds of the present invention are used in diffusion transfer processes, the processing composition if it is to be applied to the emulsion by being spread thereon in a thin layer usually includes a film-forming thickening agent. The processing composition may comprise, for example, one or more developing agents of the present invention and optionally, one or more conventional developing agents such as those enumerated above, an alkali such as sodium hydroxide or potassium hydroxide and a viscosity-increasing agent such as a high molecular weight polymer, e.g., sodium carboxymethyl cellulose, hydroxyethyl cellulose, or carboxymethyl hydroxyethyl cellulose. As noted above, in the production of silver transfer image, a silver halide solvent is employed which may be included in the processing composition, or if desired, a silver halide solvent precursor such as those disclosed in U.S. Pat. No. 3,698,898 of J. Michael Grasshoff and Lloyd D. Taylor may be disposed in a layer of the film unit. In addition to the above ingredients, the processing composition may be further modified by the inclusion of restrainers, preservatives and other components commonly employed in developer compositions. All these materials are preferably in aqueous solution.

Rather than being dissolved in the aqueous alkaline processing composition prior to application thereof to an exposed silver halide emulsion, the developing agents of the present invention may be disposed prior to exposure in the photosensitive element, e.g., by placing them in, on or behind a silver halide emulsion layer. In this instance, the processing composition containing the developing agent is formed by application of the photosensitive element of an aqueous alkaline solution capable of solubilizing the developing agent. In diffusion transfer processes, the subject developing agents may be disposed in a layer of the film unit, i.e., in a first sheet-like element comprising a photosensitive silver halide emulsion layer and/or in a second sheet-like element adapted to be superposed with said first sheet-like element but usually are contained in the processing composition. Whether the developing agent is initially disposed in the processing composition or in a layer of the film unit, e.g., in the photosensitive element, upon application of the processing composition, the developing agent is provided for processing the photoexposed silver halide material.

To illustrate their usefulness as reducing agents for silver halide, each compound (A-J) was separately evaluated by placing a few crystals of the specific compound in an amount of 10% sodium hydroxide sufficient for the crystals to dissolve therein. One drop of the respective solution was placed on "Velox" paper (a photographic printing paper containing a silver chloride emulsion) and the results noted. In every instance, the silver salt in the area of the dissolved crystals was reduced as evidenced by the appearance of a dark spot. No darkening occurred, however, where the 1N sodium hydroxide was placed on "Velox" alone.

To illustrate the utility of the above-identified compounds as photographic developing agents, a photosensitive silver iodobromide emulsion on a support was exposed to a step wedge and processed by spreading a layer of processing composition approximately 1.2 mil. thick between the exposed emulsion and a superposed image-receiving element comprising a layer of hydrolyzed cellulose acetate containing palladium sulfide nuclei carried on a transparent support. The processing composition was prepared by adding a developing agent of the present invention at a concentration of 5% by weight to the following formulation:

| | |
|---|---|
| Water | 1,000.0 g. |
| Potassium Hydroxide (Aqueous 50% w/w Solution) | 170.0 g. |
| Hydroxyethyl cellulose | 30.0 g. |
| Uracil | 50.0 g. |
| Zinc acetate | 10.0 g. |

After an imbibition period of approximately 1 minute, the developed silver halide emulsion was separated from the image-receiving element, and the maximum and minimum transmission densities were measured for the positive image.

The compounds added to the base formulation as developing agents and the density measurements for the positive image obtained with each of the compounds are set forth in Table I.

TABLE I

| Compound | Density | |
|---|---|---|
| (Formula Letter) | Maximum | Minimum |
| (C) | 1.35 | 0.22 |
| (D) | 0.25 | 0.10 |
| (E) | 1.52 | 0.07 |
| (H) | 0.84 | 0.39 |
| (I) | 2.36 | 0.16 |

It will be apparent that the relative proportions of the subject developing agents and of the other ingredients of the processing compositions may be varied to suit the requirements of a given photographic system. Also, it is within the scope of this invention to modify the formulations set forth above by the substitution of alkalies, antifoggants and so forth other than those specifically mentioned. Where desirable, it is also contemplated to include the processing compositions, other components as commonly used in the photographic art.

Since certain changes may be made in the above compositions and processes without departing from the scope of the invention herein involved, it is intended that all matter contained in the above description should be interpreted as illustrative and not limiting in any sense.

What is claimed is:

1. A photographic developer composition comprising an aqueous alkaline solution containing at least one silver halide developing agent selected from the group consisting of

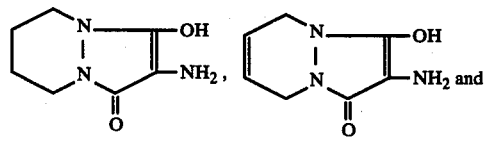

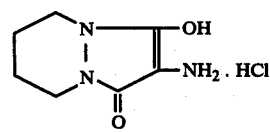

and salts thereof.

2. The developer composition as defined in claim 1 wherein said developing agent is:

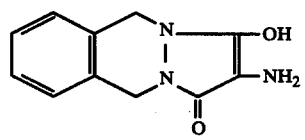

3. The developer composition as defined in claim 1 wherein said developing agent is:

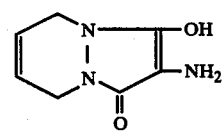

4. The developer composition as defined in claim 1 wherein said developing agent is:

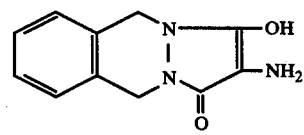

5. A method of developing a silver halide emulsion which comprises treating an exposed silver halide emulsion with an aqueous alkaline processing composition containing at least one silver halide developing agent selected from the group consisting of

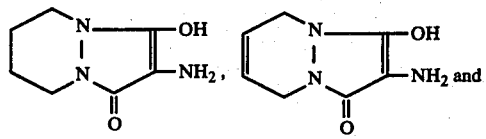

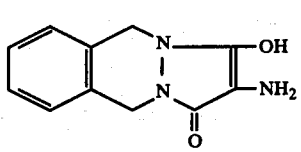

and salts thereof.

6. A method as defined in claim 5 wherein said developing agent is:

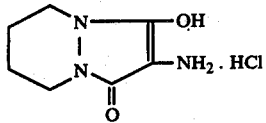

7. A method as defined in claim 5 wherein said developing agent is:

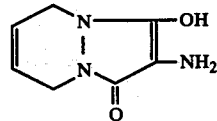

8. A method as defined in claim 5 wherein said developing agent is:

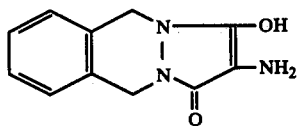

9. A photographic product comprising a support, a silver halide emulsion carried on said support and a silver halide developing agent selected from the group consisting of

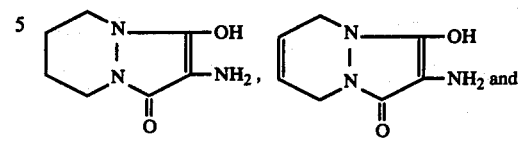

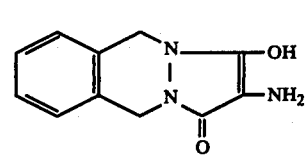

and salts thereof.

10. The product of claim 9 wherein said developing agent is:

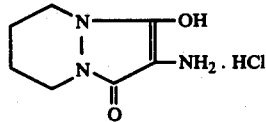

11. The product of claim 9 wherein said developing agent is:

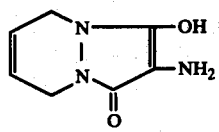

12. The product of claim 9 wherein said developing agent is:

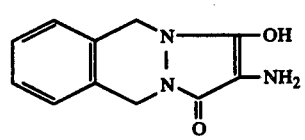

* * * * *

UNITED STATES PATENT AND TRADEMARK OFFICE
CERTIFICATE OF CORRECTION

PATENT NO. : 4,128,425                                                    Page 1 of 2

DATED : December 5, 1978

INVENTOR(S) : Richard B. Greenwald

It is certified that error appears in the above-identified patent and that said Letters Patent are hereby corrected as shown below:

On the title page, right hand column, line 1, delete "about".

On the title page, right hand column, line 4, delete "hydroalkyl" and insert ---hydroxyalkyl---.

Column 11, line 6, after "1.0" insert ---g---.

Column 12, line 61, delete "3.6" and insert ---3,6---.

Column 15, line 62, delete "solrate" and insert ---solvate---.

Column 17, line 66, after "filtered" and before "argon" insert ---under---.

Column 18, line 25, delete "alllowed" and insert ---allowed---.

Column 23, line 48, after "step" insert ---3---.

Column 24, line 11, delete "$N_4H_4 \cdot HBr$" and insert ---$N_2H_4 \cdot HBr$---.

Column 25, line 24, after "bined" and before "extracts" insert ---chloroform---.

UNITED STATES PATENT AND TRADEMARK OFFICE
CERTIFICATE OF CORRECTION

PATENT NO. : 4,128,425
DATED : December 5, 1978
INVENTOR(S) : Richard B. Greenwald It is certified that error appears in the above-identified patent and that said Letters Patent are hereby corrected as shown below:

Column 28, lines 22, after "another" and before "halide" insert ---silver---.

Signed and Sealed this

Twenty-sixth Day of February 1980

[SEAL]

Attest:

SIDNEY A. DIAMOND

Attesting Officer

Commissioner of Patents and Trademarks